RASPBERRY PLANT
Filed Nov. 19, 1973
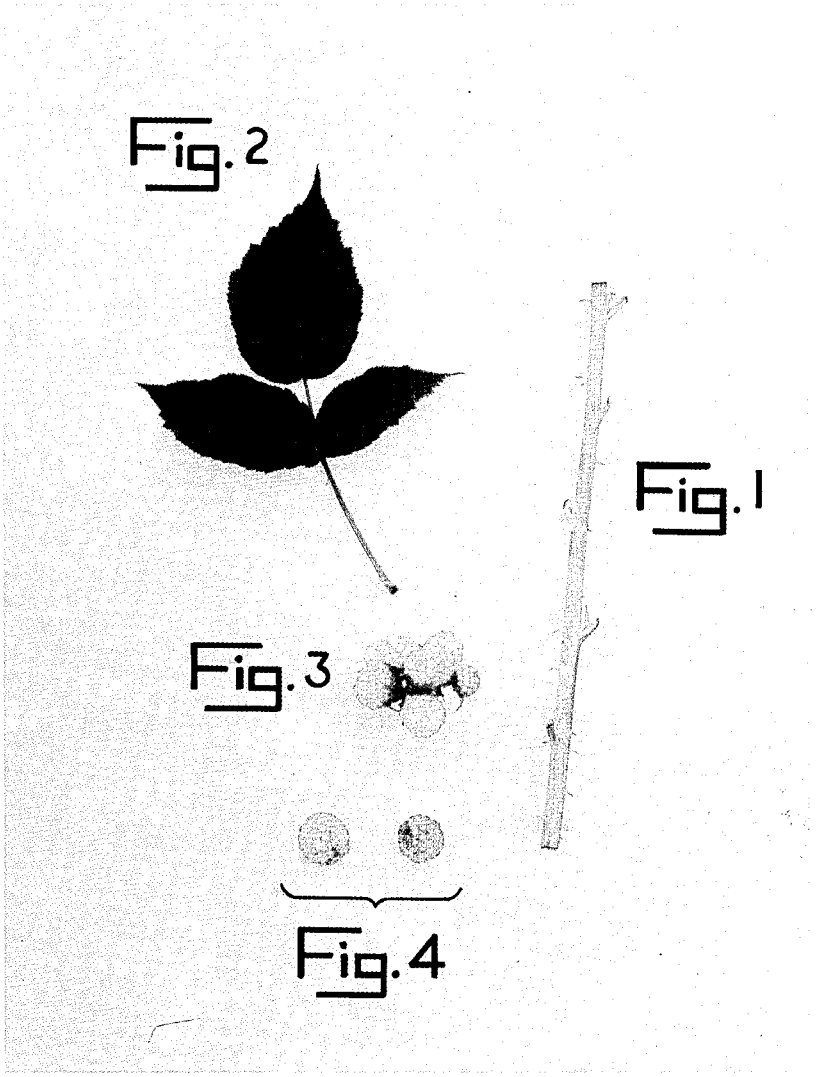

United States Patent

Plant Pat. 3,717

Patented May 13, 1975

3,717

RASPBERRY PLANT

Marion Hagerstrom, Monticello, Minn., assignor to Herschel L. Boll, Champaign, Ill.

Filed Nov. 19, 1973, Ser. No. 417,429

Int. Cl. A01h *5/03*

U.S. Cl. Plt.—46 1 Claim

My invention relates to a new and distinct variety of raspberry plant. It was discovered by me as a chance seedling, a single plant growing under a tree in an uncultivated area of my lawn at Monticello, Minn., in 1968.

Since my discovery of the original plant. I have asexually reproduced a large number of plants from the original mother plant by tip layers.

My object in the asexual propagation of the original mother plant was to determine the characteristics of the plant and of its fruit by the testing of a large number of plants. The distinguishing features of my new variety have proved to be permanent. The plant has proved itself to have unusual possibilities because of its very vigorous growth; its high productivity; and its medium-sized, yellow-to-amber colored fruit.

In the accompanying drawings:

FIG. 1 shows a section of a typical primocane.

FIG. 2 is a typical leaf in full color.

FIG. 3 shows a typical cluster of fruit.

FIG. 4 illustrates two berries of typical shape.

In general, the distinct and new variety of raspberry plant, which is the subject of my invention and discovery, is characterized by its very vigorous growth; by its high productivity; and by its medium-sized, yellow-to-amber colored fruit. These characteristics I now refer to in greater detail. Color plate references are according to Color Standards and Color Nomenclature by Robert Ridgway.

Under the conditions at Monticello, Minn., and at Champaign, Ill., my new variety of plant is spring-bearing and high in productivity. The plants are very vigorous. After a tip layer is rooted, usually several secondary laterals (about 3 to 4, and up to 7, in number, and about 3 to 4 feet in length) will develop just above the soil and will root at the tips (*Rubus occidentalis* or a yellow black-raspberry). Most plants of most varieties of black raspberries do not produce, just above the soil, secondary laterals that root at the tips unless the tips of the primary laterals are bruised. Furthermore, if they do so, these secondary laterals are only about 8 inches in length. The canes of the yellow red-raspberry or *Rubus idaeus strigosus,* such as, Amber, Golden Queen, Fallgold, Better Homes and Gardens, and Goldenwest, do not root at the tip, but are propagated by suckers. The canes of my new variety are erect and arching (*Rubus occidentalis*), while the canes of Amber, Golden Queen, Fallgold, Better Homes and Gardens, and Goldenwest, are erect or nodding at the top. The immature primocanes are light green to yellowish green in color. The mature primocanes are yellowish green to yellow, or are approximately Sulphine Yellow (Plate IV), or varying from Pyrite Yellow (Plate IV) to Sulphine Yellow (Plate IV) to Aniline Yellow (Plate IV) (except in some cases they are more greenish on the unexposed surface), depending on exposure and soil, weather, and climatic conditions. The primocanes are glaucous, having much bloom. Prickles are medium in number and in size.

The leaves are medium green in color, or are approximately Forest Green (Plate XVII), or varying from Grass Green (Plate VI) to Forest Green (Plate XVII) to Cerro Green (Plate V), depending mainly on soil fertility, but also depending on other soil conditions, exposure, and weather and climatic conditions. The leaves are medium in size. The flowers are medium in size. The date of the first blossoms in 1973 at Champaign, Ill., was May 22.

At Monticello, Minn., and at Champaign, Ill., my new variety of raspberry plant begins to mature its fruit in midseason. The date of the first picking in 1973 at Champaign, Ill. was June 19. The harvesting period is medium in length, or 10 to 14 days.

Under the conditions existing where my new variety of raspberry plant has been reproduced and tested, the fruit is yellow to amber in color (*Rubus occidentalis* or a yellow black-raspberry), or is approximately Deep Chrome (Plate III), or varying from Mustard Yellow (Plate XVI) to Deep Chrome (Plate III), to Xanthine Orange (Plate III), depending mainly on exposure, but also depending on soil, weather, and climatic conditions. The fruit is medium in size, hemispherical in shape, relatively free from crumbling, firm, less than average in juiciness, relatively sweet, and high in flavor. It is easily picked, separating readily from the receptacle. The number of berries per cluster is about 7 to 11 and the number of drupelets per berry ranges from about 30 to 50. The drupelets are medium in size with a moderate amount of pubescence and no indication of bloom between drupelets. The seeds are medium in size.

It is not claimed that my new variety of raspberry plant is especially resistant to any of the diseases; however, no virus diseases have been found on the plants of this variety to date.

The raspberry above described and the plant producing it may vary in slight details, depending on soil, weather, and climatic conditions.

What I claim is:

1. A new and distinct variety of raspberry plant substantially as herein shown and described, characterized by its very vigorous growth; by its high productivity; and by its medium-sized, yellow-to-amber colored fruit.

References Cited

Bountiful Ridge Nurseries, 1962–3 catalog, Princess Anne, Md., p. 43 relied on.

Spring Hill Nurseries, Spring 1969 catalog, Tipp City, Ohio, pp. 34–5 relied on.

ROBERT E. BAGWILL, Primary Examiner